United States Patent [19]

Swager et al.

[11] Patent Number: 5,519,147
[45] Date of Patent: May 21, 1996

[54] DERIVATIZED POLYTHIOPHENES AND DEVICES COMPRISING SAME

[75] Inventors: Timothy M. Swager, Wynnewood; Michael J. Marsella, Philadelphia, both of Pa.

[73] Assignee: Trustees of the University of Pennsylvania, Philadelphia, Pa.

[21] Appl. No.: 393,235

[22] Filed: Feb. 23, 1995

Related U.S. Application Data

[63] Continuation of Ser. No. 166,552, Dec. 14, 1993, abandoned.

[51] Int. Cl.$^6$ .................... C07D 409/02; C07D 333/32; C07D 327/00; C08G 75/00
[52] U.S. Cl. ........................ 549/59; 549/62; 549/4; 549/10; 549/11; 549/12; 528/380
[58] Field of Search .................... 549/59, 60, 62, 549/43, 45, 352, 348, 349, 352, 12, 11, 10; 526/256; 528/380

[56] References Cited

U.S. PATENT DOCUMENTS

| | | | |
|---|---|---|---|
| 4,909,959 | 3/1990 | Lemaire et al. | 526/256 |
| 4,992,559 | 2/1991 | Kathirgamanathan et al. | 549/65 |
| 5,111,327 | 5/1992 | Blohm et al. | 526/256 |
| 5,132,049 | 7/1992 | Garreau et al. | 526/256 |
| 5,200,041 | 4/1993 | Simonet et al. | 204/78 |
| 5,204,424 | 4/1993 | Roncali et al. | 526/256 |

OTHER PUBLICATIONS

Bidan, G., "Electroconducting conjugated polymers: new sensitive matrices to build up chemical or electrochemical sensors," *Sensors and Actuators B*, 6:45–56, 1992.

Cram, D. J., "The Design of Molecular Host, Guests, and Their Complexes," *Angew. Chem. Int. Ed. Engl.*, 27:1009–1020, 1988.

Espenscheid et al., "Sensors from Polymer Modified Electrodes," *J. Chem. Soc., Faraday Trans. I*, 82:1051–1070, 1986.

Gourdon et al., "Molecular Switching from Conformational Change," *New J. Chem.*, 16:953–957, 1992.

Heywang et al., "Poly(alkylenedioxythiophene)s–New, Very Stable Conducting Polymers," *Adv. Mater.*, 4:116–118, 1992.

Kittlesen et al., "Chemical Derivatization of Microelectrode Arrays by Oxidation of Pyrrole and N–Methylpyrrole: Fabrication of Molecule–Based Electronic Devices," *J. Am. Chem. Soc.*, 106:7389–7396, 1984.

Monreal et al., "The Use of Polymer Materials as Sensitive Elements in Physical and Chemical Sensors," *Sensors and Actuators*, 12:129–144, 1987.

Roncali, J., "Conjugated Poly(thiophene): Synthesis, Functionalization, and Applications," *Chem. Rev.*, 92:711–738, 1992. (I).

Roncali et al., "Electrosynthesis of conducting polypseudo–crown ethers from substituted thiophenes," *J. Electroanal. Chem.*, 278:373–378, 1990. (II).

Thackeray et al., "Chemically Responsive Microelectrochemical Devices Based on Platinized Poly(3–methylthiphene): Variation in Conductivity with Variation in Hydrogen, Oxygen or pH in Aqueous Solution," *J. Phys. Chem.*, 90:6674–6679, 1986.

Thackeray et al., "Poly(3–methylthiophene)–Coated Electrodes: Optical and Electrical Properties as a Function of Redox Potential and Amplification of Electrical and Chemical Signals Using Poly(3–methylthiophene)–Based Microelectrochemical Transistors," *J. Phys. Chem.*, 89:5133–5140, 1985.

Thienpont et al., "Saturation of the Hyperpolarizability of Oligothiophenes," *Physical Review Letters*, 65:2141–2144, 1990.

Van Dort et al., "Poly(3,4–Dibutoxythiophene Vinylene): A New Processable Conducting Polymer with Unusual Optical Properties, Synthesis, Characterization and Stability," *Synthetic Metals*, 41–43:2305–2308, 1991.

Zotti, G., "Electrochemical sensors based on polyconjugated conducting polymers," *Synthetic Metals*, 51:373–382, 1992.

*Primary Examiner*—Richard L. Raymond
*Assistant Examiner*—Deborah Lambkin
*Attorney, Agent, or Firm*—Woodcock, Washburn, Kurtz, Mackiewicz & Norris

[57] ABSTRACT

Novel polythiophene derivatives are provided along with sensing devices comprising such derivatives in a layer disposed upon a substrate. In preferred embodiments, the polythiophene derivatives bear crown ether moieties covalently bound to 3 positions of adjacent thiophene units.

19 Claims, 3 Drawing Sheets f. Me₃SnCl, THF.
g. 5,5'-dibromo-2,2'-bithiophene, PdCl₂(AsPh₃)₂, THF, reflux.
h. 0.5eq. Mg*, 0.5% NiCl₂dppp, Et₂O, 0°C (98%).
i. 2eq. NBS, DMF/MeOH (95%).
j. NBS, benzoyl peroxide, AIBN, benzene, reflux (78%).
k. MOCH₂―(CH₂OCH₂)ₙ₊₂―CH₂OM for z=1, M=Na⁺, DME (55%); for z=2, M=K⁺, THF (18%).

DERIVATIZED POLYTHIOPHENES AND DEVICES COMPRISING SAME

GOVERNMENT SUPPORT

This work has been supported by National Science Foundation Grant DMR-9258298 and DMR-9120668.

This is a continuation of application Ser. No. 08/166,552, filed on Dec. 14, 1993, now abandoned.

FIELD OF THE INVENTION

This invention relates to materials that are useful in the fabrication of chemical sensing devices. This invention also relates to methodologies whereby organic compounds are derivitized to find use in such devices. In one preferred embodiment, the invention relates to crown ether-containing polythiophenes that exhibit ion-selective chemical sensitivity.

BACKGROUND OF THE INVENTION

The concentrations of metal ions in various media are extensively measured both in the biological sciences and in the health care industry. Several methodologies exist for taking these measurements, including the use of ion selective electrodes, ion responsive dyes, and ion sensitive field effect transistors (IFETS). (See, e.g., Supramolecular Chemistry I—Directed Synthesis and Molecular Recognition, Weber, E., Ed., Springer-Verlag, New York, 1993.) However, ion selective electrodes have the disadvantage that they are not easily miniaturized, and IFETS and ion responsive dyes lack the high sensitivity necessary for trace analysis.

Conducting polymers (CPs) have been the focus of considerable interest because they combine the relatively low cost and ease of manufacturing of polymers with the conductive properties of metals and semiconductors. Moreover, the conductivity of conducting polymers is highly responsive to both conformational and electrostatic perturbations. For example, it is well known that twisting a conducting polymer's backbone from planarity can result in a conductivity drop as high as 105 or greater. See, e.g., Handbook of Conducting Polymers, Skotheim, T. J., Ed., Dekker, New York, 1986. Hence, conductivity changes in conducting polymers provide a large dynamic range which, if harnessed effectively, can result in very sensitive sensory materials. Such conductivity changes easily can be monitored and miniaturized. See, e.g., Kittlesen, et al., *J. Am. Chem. Soc.* 1984, 106, 7389.

Conducting polymer-based sensors have been previously reported. (See, e.g., Thackeray, et al., *J. Phys. Chem.* 1986, 90, 6674; Zotti, *Synthetic Metals* 1992, 51, 373.) However, known polymer-based sensors are chemically irreversible and cannot detect a time dependent signal in real time. This is a serious deficiency where it is desired to measure stimuli which vary over time, such as in the monitoring of electrolyte concentrations in bodily fluids. Additionally, there are no systems at present that can be easily modified to detect a variety of chemical species.

Substituted polythiophenes are an ideal choice for sensory materials due to their ease of structural modifications, high conductivity, and environmental stability. In addition, recent studies have shown the conductivity of these materials to be highly sensitive to the nature and regiospecificity of covalently bound sidechains, indicating that small conformational changes produce large effects. (See, e.g., Roncali, *J. Chem. Rev.* 1992, 92, 711; Heywang, et al., *Adv. Mater.* 1992, 4, 116; McCullough, et al, *J. Am Chem. Soc.* 1993, 115, 4910.) However, previous attempts to develop polythiophene-based sensory materials showed no ion-selective electrochemical response. (see, Sable, et al., *Electrochemica Acta* 1991, 36, 15.)

Consequently, there remains a need in the art for conductive polymers whose conductivities change reversibly in response to a variety of chemical species.

OBJECTS OF THE INVENTION

It is one object of the present invention to provide novel, conductive polythiophenes.

It is another object of the invention to provide derivatized polythiophenes whose conductivities change measurably and selectively in response to metal ions and other chemical species.

It is a further object to provide materials that include such derivatized polythiophenes.

It is yet another object to provide sensing devices that include such materials.

SUMMARY OF THE INVENTION

These and other objects are satisfied by the present invention, which provides novel polythiophene derivatives and sensing devices containing such derivatives.

In certain embodiments, the polythiophene derivatives have formula (1):

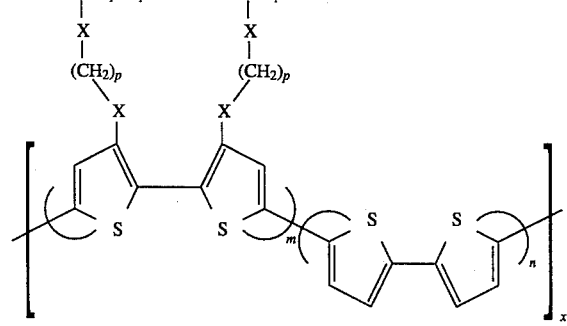

wherein:

each X is O, $NR_3$, or S;

$R_3$ is alkyl having 1 to about 5 carbon atoms;

Y is $(CH_2)_p$, aryl having 6 to about 14 carbon atoms, or calixarenyl having 18 to about 200 carbon atoms;

m is 1 to about 5;

n is 0 to about 5;

each p is, independently, 1 to about 5;

each q is, independently, 0 to about 5; and x is 1 to about 1000. In preferred embodiments, each X is O, Y is $(CH_2)_2$, n is 0 or 1, m is 1, each p is 2, q is 1, r is 0, and x is 1 to about 10.

In another aspect, the invention provides compounds that find use in preparing such derivatized polythiophenes. In one embodiment, the invention provides compounds having formula (2):

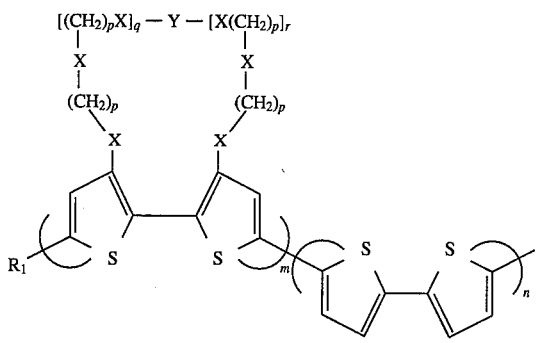

(2)

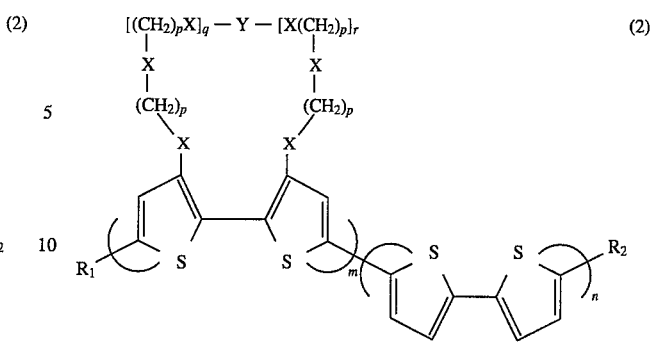

(2)

wherein $R_1$ and $R_2$ are, independently, H, Cl, Br, I, Li, $Sn(R_3)_3$, or $Si(R_3)_3$, n is 0 or 1, and m is 1.

The present invention further provides sensing devices that include novel polythiophene derivatives. In general, the devices comprise a layer that contains at least one polythiophene derivative of the invention disposed upon a substrate. The layer can contain the derivative in pure or substantially pure form or in combination with other chemical compounds such as known synthetic organic polymers.

The invention also provides methods for preparing sensors comprising the steps of providing a substrate and placing upon said substrate at least one layer that includes at least one polythiophene derivative according to the invention.

Also provided are methods for using the sensors of the invention, comprising contacting the polythiophene containing layer to a chemical species and then determining any resulting change in conductivity for the polythiophene.

BRIEF DESCRIPTION OF THE DRAWINGS

The numerous objects and advantages of the present invention may be better understood by those skilled in the art by reference to the accompanying figures, in which.

DETAILED DESCRIPTION OF THE PREFERRED EMBODIMENTS

Figure 1:
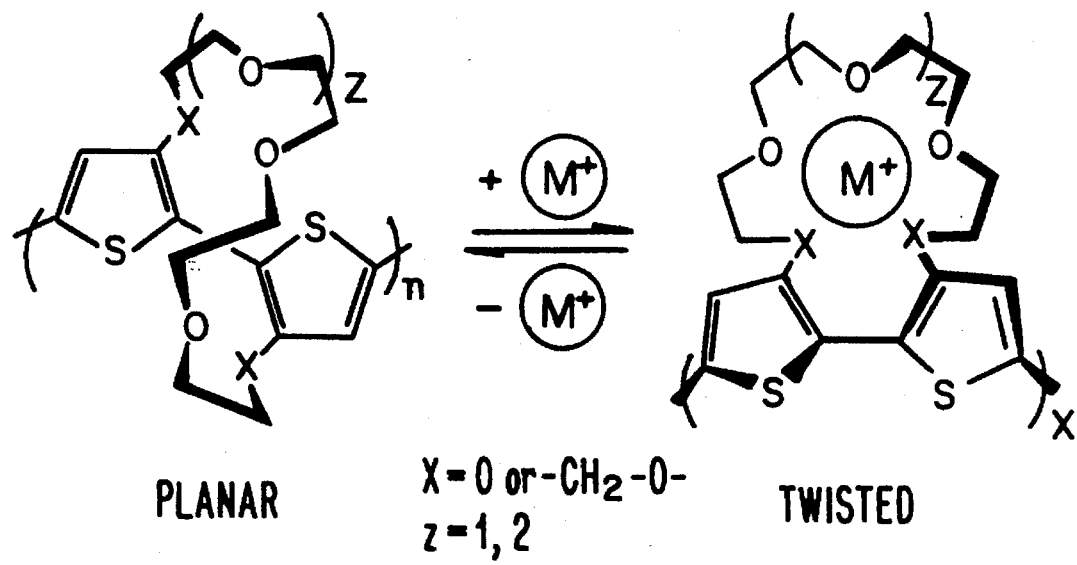
FIG. 1 shows the reversible manner in which compounds of the invention bind metal ions.

This invention provides new compounds and sensing devices useful in the detection of a variety of chemical species. In preferred embodiments, the detected species is an ion, that is, a chemical moiety that bears a net positive or net negative electrical charge. Preferred ions for detection are metal ions, particularly ions of metals belonging to Groups I and II of the Periodic Table. Particularly preferred are calcium ions, magnesium ions, and ions of the alkali metals (i.e., lithium, potassium, sodium, cesium, and rubidium).

According to one embodiments of the invention, somewhat monomeric bithiophene compounds are provided having the formula (2):

Each X can be independently selected to be O, $NR_3$, or S wherein $R_3$ is alkyl having 1 to about 5 carbon atoms. The term alkyl is intended to denote both straight chain and branched hydrocarbon moieties such as methyl ($CH_3$), methylene ($CH_2$), and ethyl ($CH_2CH_3$) groups. X preferably is O.

Y can be $(CH_2)_p$, aryl having 6 to about 14 carbon atoms, or calixarenyl having 18 to about 200 carbon atoms;. The term aryl is intended to denote monocyclic and polycyclic aromatic groups including, for example, phenyl, naphthyl, benzyl, and xylyl groups and substituted derivatives thereof. Y preferably is $(CH_2)_2$ or phenyl. Additionally, the aryl portion of Y can be substituted at one or more positions to afford additional degrees of selectivity and specificity in the binding of a chemical species. The term calixarenyl is intended to denote polycyclic groups derived from one or more calixarenes. A wide variety of functionalized calixarenes suitable for use in accordance with the invention are known in the art, as are methods for their preparation. Indeed, the organic chemistry of calixarenes is extensive (see, e.g., *Gutsche, Calixarenes, Royal Society of Chemistry* (1989); *Calixarenes: A Versatile Class of Macroscopic Compounds*, Vicens and Klewer, eds., Academic Publishers (1991); Cram, *Science* 1983, 219, 1177). A number of calixarene derivatives are disclosed in U. S. patent application Ser. No. 08/011,301, filed Jan. 29, 1993, which is incorporated herein by reference. One representative calixarenyl group according to the invention has formula (3) wherein $R_B$ is H or a group that is electron,withdrawing relative to hydrogen.

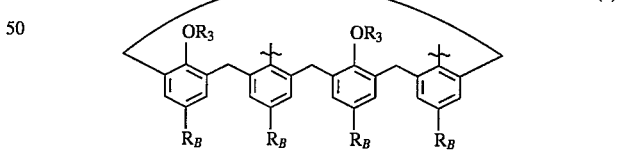

(3)

$R_1$ and $R_2$ are chosen to facilitate synthesis of the polythiophene compounds of the invention. It will be recognized, therefore, that $R_1$ and $R_2$ can be selected from a wide variety of groups known in the art. For example, $R_1$ and $R_2$ can be independently selected from H, Cl, Br, I, Li, $Sn(R_3)_3$, or $Si(R_3)_3$, although $R_1$ and $R_2$ preferably are the same. Subscripts p likewise can be independently selected but preferably are the same. Preferably, p is 1 or 2.

In one preferred embodiment, bithiophene compounds having formula (2) are polymerized to produce polythiophene derivatives having formula (1):

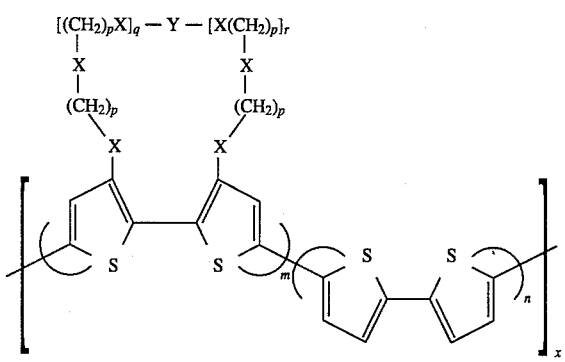

wherein X, Y, $R_3$, n, m, p, q, and r are as defined above. The polythiophene derivatives of the invention can include up to about 1000 monomeric units (i.e., x can be 1 to about 1000). Preferably, x is 1 to about 100, more preferably 1 to about 15.

The polythiophenes Of invention can be substituted at one or more of the thiophene 4- or 4'-positions or other positions within the compounds of the invention. Such substitutions may be desirable, for example, to influence the electronic properties of the polymeric chain either directly or to introduce steric constraints. Due to steric constraints, substitution with relatively small groups (e.g., fluoro and methyl groups) are believed to be preferred. Such substitutions are envisioned to provide inductive effects, modifying the local electronic structure of the polythiophene chain. The optimal substituent for a given stimulus can be determined by routine experimentation. It also may be desirable to introduce slightly larger groups (e.g., ethyl groups) as substituents on the polythiophene chain to introduce additional steric constraints for control either the planarity of the polythiophene chain in the absence of a chemical stimulus or the ability of the chain to rotate out of plane in response to stimulus binding.

It will also be appreciated that each thiophene unit in the polythiophene derivatives of the invention need not bear a macrocyclic moiety. Indeed, it may prove desirable to incorporate into the polymeric chain thiophene units having no macrocyclic component.

As will be recognized, compounds having formulas (1) and (2) include two general structural components: a thiophene moiety (e.g., a thiophene unit or covalently bound thiophene units) and a macrocyclic moiety (i.e., an exocyclic tether joining the different thiophene positions). Macrocyclic moieties preferably span the 3 and 3' positions of a bithiophenic monomer of the invention, but also may span other positions of the same or different thiophene units. In terms of ion selectivity, it appears that polythiophene derivatives having relatively smaller macrocyclic moieties generally give the largest response for relatively small ions such as Na+ and that polythiophene derivatives having larger macrocyclic moieties generally are more sensitive for larger ion such as K+.

In the polythiophene derivatives of the invention the macrocyclic moieties are believed to bind or chelate specific chemical species to be detected and, thereby, induce a change in the local electronic structure of the polythiophene derivative of formula (1) or (2). This is believed to be accompanied by a decrease in pi-orbital overlap between thiophene rings and, hence, a decrease in the extent of conjugation. Also, when X=0 the ability of the oxygens at the 3-position to donate electron density into the polymer backbone appears to be limited due to lone pair electron interactions with the bound chemical species. Both effects result in a hypsochromic shift and an increase in the band gap of the polymer. Moreover, stimulus binding is believed to induce an out-of-plane twisting of the polythiophene chain, shown in FIG. 1. Such twisting of the chains is believed to disrupt the electrical conductivity of the polymer. Any change in conductivity is detected and translated into changes in the concentration of the stimulus.

Twisting of the polymer's backbone from planarity also is believed to reduce its effective conjugation length. Accordingly, the polymers of the invention exhibit large ionochromic responses which are easily detected visually.

Sensing devices also are provided in accordance with the invention. The term sensor or sensing device, when used in the context of the invention, refers to devices that are capable of producing measurable, steady-state responses to one or more stimuli of interest.

Figure 2:
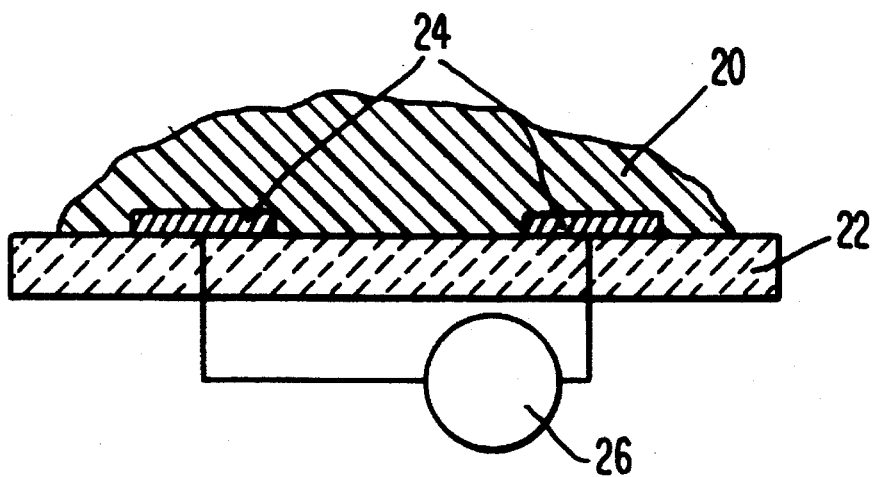
FIG. 2 shows a sensing device according to the invention.

FIG. 2 shows a sensing device according to the invention wherein a layer 20 containing a polythiophene derivative is disposed on an insulating substrate 22. The substrate bears on its surface at least two contacts 24 that are in electrical communication with one another. Interposed between the contacts and in electrical communication therewith is a suitable means 26 for measuring resistance. Those skilled in the art will appreciate that the spirit of the invention may be implemented in different forms. Typically, the resistance of the polythiophene is monitored as the observed signal either by measuring the current with a fixed voltage drop across the polymer or by measuring a voltage drop with fixed current. As will be recognized, such devices can be employed in series or in parallel with other sensors or electronic elements. Upon binding of a specific stimulus by the macrocyclic moieties of the polymer, either a conformational change, or, depending upon which polymer is used, an inductive electronic effect is introduced into the polymer backbone. Consequently, the conductivity of the polymer changes and this is detected as either a change in current or a change in voltage across the electrical contacts.

The sensors of the present invention find use in the medical arts in, for example, the monitoring of electrolyte concentrations of bodily fluids. Such sensors also can be used to detect ions or organic molecules which may be present in the form of contaminants and, thus, will find use in the manufacturing and quality control fields. The sensors of the invention also can be used for other applications such as, for example, in the monitoring of chemical processes.

The polythiophene-based sensors of the invention can be constructed to detect a wide variety of different stimuli. The only requirement for such sensors is that the macrocyclic component of the polythiophene induce a conformational change or electronic perturbation in the polythiophene backbone upon binding a stimulus of interest. Useful macrocyclic components preferably include crown ethers. As will be recognized, the specificities crown ethers for many chemical species are well known in the art. See, e.g., Hiraoka, Crown Compounds: Their Characteristics and Applications, Elsevier Sci. Pub., 1982. The invention, however, is not limited to compounds containing crown ether macrocyclic components, but includes compounds having any macrocyclic components set forth above that binds a stimulus of interest and thereby effects a conformational change, an inductive electronic perturbation to the polythiophene backbone, or a reduction/oxidation (redox) process. The term polythiophene backbone, when used in connection with the present invention refers to a polymeric network of thiophene molecules covalently bound to one another at 2 and 2' positions.

Figure 3A:
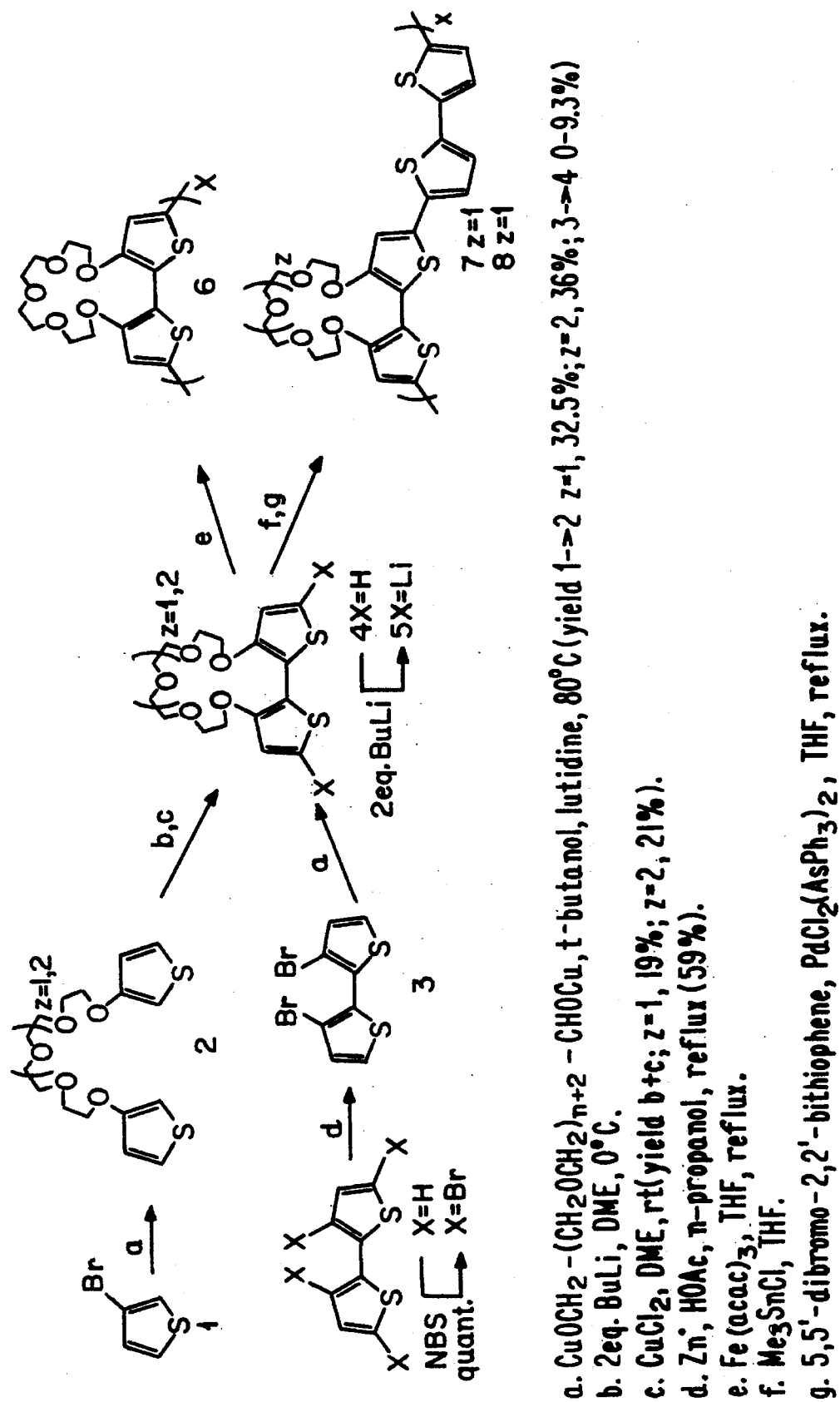
FIGS. 3A and 3B shows exemplary synthetic routes according to the invention.
Figure 3B:
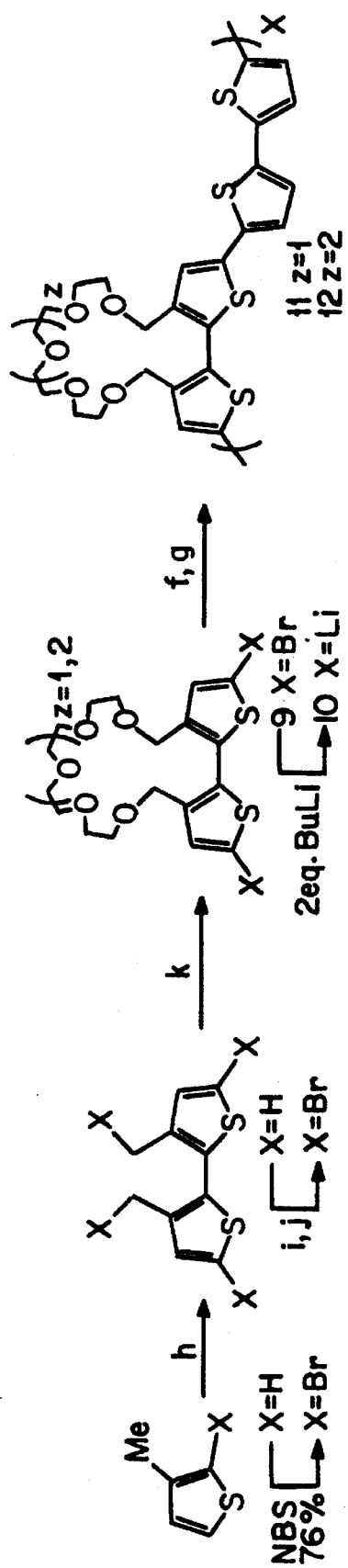

The polythiophene derivatives of the invention generally can be prepared by methods known in the art, including electrochemical oxidation, chemical oxidation, and chemical coupling reactions. FIGS. 3A and 3B shows a number of exemplary syntheses. Two routes to monomer 4 were investigated utilizing copper catalyzed alkoxylation to directly attach the terminal oxygens of a polyether tether to the 3-positions of thiophene rings. The first involves alkoxylating 1 and then forming bithiophene containing macrocycle by selectively coupling 2 at its 2,2'-thiophene positions. The second involves alkoxylating 3 to form the macrocycle directly. The latter route gives variable low yields and the major product is bithiophene, showing that reductive dehalogenation predominates under these conditions. The former proceeds smoothly to give 2 (z=1, z=2) in 33% and 36% yields, respectively. Treatment of the dilithio species of 2 in dimethyl ether with copper (II) chloride gave the desired macrocycle 4 in approximately 20% yield.

Polymer 6 was prepared by a method whereby dilithiated monomer 5 is formed and then reacted with Fe(acac)$_3$. In this Fe(III) polymerization, insoluble Fe(acac)$_2$ is separated by filtration to produce materials free of the iron salts which typically plague FeCl$_3$ oxidative polymerizations. Additionally, $^1$H NMR showed no evidence of the deleterious α-β coupling which is usually observed in oxidative polymerizations of thiophenes. After precipitating 6 in methanol, the degree of polymerization of the soluble (i.e., low molecular weight) portion was determined by $^1$H NMR integration of the two doublets resulting from the disubstituted thiophene end groups to contain ten thiophene units.

FIG. 3B shows the synthetic route to polythiophene derivatives 11 and 12, wherein methylene spacers are inserted between the polythiophene moiety and the macrocyclic moiety. The methylene spacers increase the size of the macrocyclic cavity and are believed to prevent electron donation from the macrocyclic moiety to the thiophene ring. As discussed below, only small responses are detectable for the compounds in which atoms X of the macrocyclic moiety are not connected directly to the polythiophene residues.

Stills coupling methodology also was used to prepared polythiophenes according to the invention. (See, Heck, Palladium Reagents in Organic Synthesis Academic Press, 1985; Stille, *Angew. Chem. Int. Ed. Engl.* 1986, 25, 508.) In this case, the dilithio species of 5 and 10 are reacted in situ with trimethyltin chloride and then subjected to palladium catalyzed cross-coupling with 5,5'-dibromo-2,2'-bithiophene. The molecular weights produced in this procedure were most likely solubility limited since these copolymers precipitated during the course of the reaction. The molecular weights as determined by GPC relative to polystyrene standards were determined to be 2800, 3700, 2000, and 1900 for polymers 7, 8, 11, and 12 respectively. However, the absolute molecular weights may be higher since the absolute molecular weight determined by NMR end group analysis for 6 shows the true molecular weight (1800) to be almost double that determined by GPC (960).

The relative association constants of compounds having formula (2) were measured for K+, Na+, and Li+ using standard picrate extraction techniques generally in accordance with Koenig, et al., *J. Am. Chem. Soc.* 1979, 101, 3553. For comparative purposes, the association energies for 18-crown-6 also were measured. The binding constants for all monomers were on the order of 10$^3$ times lower than that observed for K+ with 18-crown-6. Monomer 4 bound approximately twice as effectively as the methylene spaced monomer 9.

Ionochromic effects were measured in 0.1M salt solutions in acetonitrile and the results are shown in Table 1. Polymers 6, 7, and 8 show large shifts in λmax with the appropriate ion. Because these shifts occur in the visible region, dramatic color changes are observed. As anticipated, polymers 6 and 7 show the largest shift for sodium, and 8 is most responsive to potassium. The large magnitude of the shift despite the low binding constants for the corresponding monomers likely is attributable to the additive effect of destroying conjugation at several points along a highly conjugated system. This is supported by the fact that copolymer 7, in which the number of twisting sights has been reduced, shows a smaller shift than its corresponding homopolymer, 6. The poor ionochromic activity of polymers 11 and 12 is not surprising considering their poor binding affinity (which results in failure of the twist-inducing mechanism) and the loss of electrostatic interaction between the terminal oxygens of the polyether tether and polymer backbone.

TABLE 1

| Polymer | λmax (nm) | K+ | Na+ | Li+ |
|---|---|---|---|---|
| 6 | 497 | 22 | 91 | 46 |
| 7 | 510 | 10 | 63 | 15 |
| 8 | 524 | 45 | 30 | 13 |
| 11 | 434 | −4 | 3 | 3 |
| 12 | 432 | 1 | 3 | 4 |

Those skilled in the art will appreciate that numerous changes and modifications may be made to the preferred embodiments of the invention and that such changes and modifications may be made without departing from the spirit of the invention. For example, by the implementation of known molecular recognition principles, the compounds disclosed herein can be modified to produce conducting polymers which are responsive to numerous chemical entities. It is therefore intended that the appended claims cover all such equivalent variations as fall within the true spirit and scope of the invention.

What is claimed is:

1. A compound having formula:

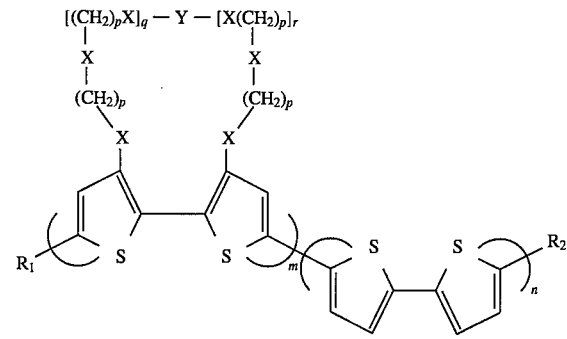

wherein:

R$_1$ and R$_2$ are, independently, H, Cl, Br, I, Li, Sn(R$_3$)$_3$, or Si(R$_3$)$_3$;

X is O, or S;

Y is (CH$_2$)$_p$, unsubstituted aryl having 6 to about 14 carbon atoms, or calixarenyl having 18 to about 200 carbon atoms;;

m is 1;

n is 0 or 1;

each p is, independently, 1 to about 5;

q is, independently, 0 to about 5; and r is, independently, 0 to about 5.

2. The compound of claim 1 wherein each X is O.

3. The compound of claim 1 wherein each X is S.

4. The compound of claim 1 wherein Y is (CH$_2$)$_2$.

5. The compound of claim 1 wherein Y is phenyl.

6. The compound of claim 1 wherein R$_1$ and R$_2$ both are H, Br, or Li.

7. A compound having formula:

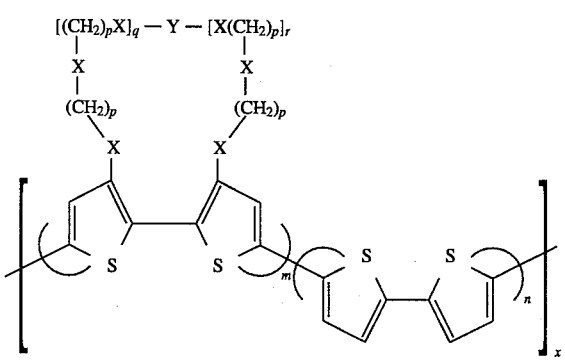

wherein:

X is O, or S;

Y is (CH$_2$)$_p$, unsubstituted aryl having 6 to about 14 carbon atoms, or calixarenyl having 18 to about 200 carbon atoms;

each m is, independently, 1 to about 5;

each n is, independently, 0 to about 5;

each p is, independently, 1 to about 5;

each q is, independently, 0 to about 5;

each r is, independently, 0 to about 5; and x is 1 to about 1000.

8. The compound of claim 7 wherein each X is O.

9. The compound of claim 7 wherein each X is S.

10. The compound of claim 7 wherein m is 1 and n is 0.

11. The compound of claim 7 wherein n is 1 and m is 1.

12. The compound of claim 7 wherein x is 1 to about 15.

13. The compound of claim 7 wherein p is 2.

14. The compound of claim 7 wherein q is 1.

15. The compound of claim 7 wherein r is 0.

16. The compound of claim 1 wherein Y is (CH$_2$)$_2$.

17. The compound of claim 1 wherein Y is phenyl.

18. A compound having formula:

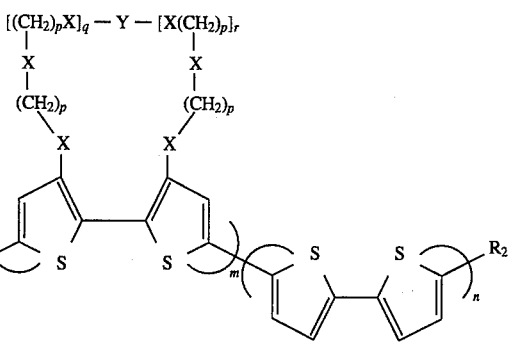

wherein:

R$_1$ and R$_2$ are, independently, H, Cl, Br, I, Li, Sn(R$_3$)$_3$, or Si(R$_3$)$_3$;

X is O, or S;

Y is (CH$_2$)$_p$, unsubstituted aryl having 6 to about 14 carbon atoms, or calixarenyl having 18 to about 200 carbon atoms;

m is 1;

n is 1;

each p is, independently, 1 to about 5;

q is, independently, 0 to about 5; and r is, independently, 0 to about 5.

19. A compound having formula:

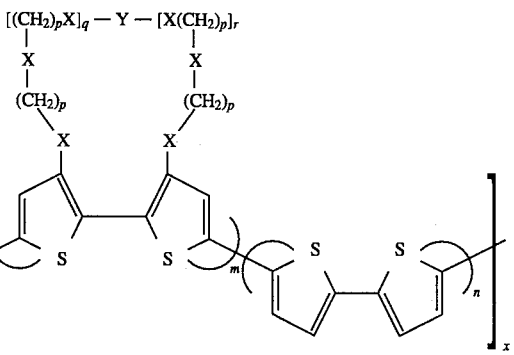

wherein:

X is O, or S;

Y is (CH$_2$)$_p$, unsubstituted aryl having 6 to about 14 carbon atoms, or calixarenyl having 18 to about 200 carbon atoms;

each m is, independently, 1 to about 5;

each n is, independently, 1 to about 5;

each p is, independently, 1 to about 5;

each q is, independently, 0 to about 5;

each r is, independently, 0 to about 5; and x is 1 to about 1000.

* * * * *

UNITED STATES PATENT AND TRADEMARK OFFICE
CERTIFICATE OF CORRECTION

PATENT NO. : 5,519,147  Page 1 of 2
DATED : May 21, 1996
INVENTOR(S) : Timothy M. Swager et al It is certified that error appears in the above-identified patent and that said Letters Patent is hereby corrected as shown below:

Col. 1, line 42, "105" should be --$10^5$--.

Col. 5, line 20, "Of" should be ---of-.

Col. 6, line 17, delete "20" and insert --$\underline{20}$--

Col. 6, line 18, delete "22" and insert --$\underline{22}$--

Col. 6, line 19, delete "24" and insert ---$\underline{24}$--

Col. 7, line 3, delete "4" and insert --$\underline{4}$--.

Col. 7, line 7, delete "1" and insert --$\underline{1}$--.

Col. 7, line 8, delete "2" and insert -$\underline{2}$-.

Col. 7, line 9, delete "3" and insert --$\underline{3}$--.

Col. 7, line 13, delete "2" and insert --$\underline{2}$--.

Col. 7, line 14, delete "2" and insert --$\underline{2}$--.

Col. 7, line 16, delete "4" and insert --$\underline{4}$--.

Col. 7, line 18, delete "5" and insert --$\underline{5}$--.

Col. 7, line 24, delete "6" and insert --$\underline{6}$--.

Col. 7, line 30, delete "11" and "12" and insert --$\underline{11}$-- and --$\underline{12}$--.

UNITED STATES PATENT AND TRADEMARK OFFICE
CERTIFICATE OF CORRECTION

PATENT NO. : 5,519,147
DATED : May 21, 1996
INVENTOR(S) : Timothy M. Swager et al It is certified that error appears in the above-identified patent and that said Letters Patent is hereby corrected as shown below:

Col. 7, line 38, Stills should be -Stille-.

Col. 7, line 42, delete "5" and "10" and insert -$\underline{5}$- and -$\underline{10}$-.

Col. 7, line 53, delete "6" and insert -$\underline{6}$-.

Col. 7, line 67, delete "6", "7" and "8" and insert --$\underline{6}$-- --$\underline{7}$-- and --$\underline{8}$--.

Col. 8, line 3, delete "6" and "7" and insert -$\underline{6}$- and -$\underline{7}$-

Col. 8, line 9, delete "7" and insert -$\underline{7}$-.

Col. 8, line 11, delete "6" and insert --$\underline{6}$--.

Col. 8, claim 1, line 61, insert the following:
--$R_3$ is alkyl having 1 to about 5 carbon atoms--.

Col.10, claim 19, line 48, insert the following:
--$R_3$ is alkyl having 1 to about 5 carbon atoms--.

Signed and Sealed this

Ninth Day of March, 1999

Q. TODD DICKINSON

*Attest:*

*Attesting Officer*    Acting Commissioner of Patents and Trademarks